United States Patent [19]

Taki et al.

[11] 4,325,942

[45] Apr. 20, 1982

[54] UBIDECARENONE COMPOSITIONS HAVING ENHANCED ABSORPTION PROPERTIES

[75] Inventors: Kazuo Taki, Komae; Hideo Takahira, Sakado, both of Japan

[73] Assignee: Eisai Co., Ltd., Tokyo, Japan

[21] Appl. No.: 169,194

[22] Filed: Jul. 15, 1980

[30] Foreign Application Priority Data

Jul. 25, 1979 [JP] Japan .................................. 54-93636

[51] Int. Cl.$^3$ .............................................. A61K 37/48
[52] U.S. Cl. ...................................... 424/94; 424/365
[58] Field of Search .................................. 424/94, 365

[56] References Cited

U.S. PATENT DOCUMENTS

| | | | |
|---|---|---|---|
| 3,317,381 | 5/1967 | Umehara | 424/94 |
| 3,426,125 | 2/1969 | Shigeta et al. | 424/94 |
| 3,534,137 | 10/1970 | Matsumura et al. | 424/94 |
| 3,560,612 | 2/1971 | Matsumura et al. | 424/94 |
| 3,808,330 | 4/1924 | Ohtake et al. | 424/94 |

*Primary Examiner*—Leonard Schenkman
*Attorney, Agent, or Firm*—Wenderoth, Lind & Ponack

[57] ABSTRACT

A novel ubidecarenone composition comprising ubidecarenone and higher fatty acid(s) or monoglyceride(s) of higher fatty acid(s), or a mixture thereof, which has improved absorptivity through the lymphatic duct.

4 Claims, No Drawings

UBIDECARENONE COMPOSITIONS HAVING ENHANCED ABSORPTION PROPERTIES

This invention relates to a ubidecarenone composition having improved absorptivity.

It has been previously known that ubidecarenone is mainly absorbed through the lymphatic duct, as oil-soluble vitamins. Ubidecarenone is however poorly absorbed. An experiment for absorption of ubidecarenone using rats shows that the absorptivity for 48 hours amounts to only 1.0%, when the ubidecarenone is administered by dissolving in sesame oil or in bile salt solution, and the absorptivity amounts to at most 1.5% even when dissolved in HCO-60 [Chem. Pharm. Bull. 15 (20) 2585 (1972)].

In the prior art, the efforts toward the production of an oil-soluble drug preparation were solely made directing to dissolve, emulsify or disperse the drug on its administration. Thus, the processes which have previously been employed for the preparations are, for example, those of dissolving the preparations in a vegetable oil such as sesame oil, peanut oil, olive oil, or of emulsifying or dispersing with a natural polymer such as gum arabic, hydrolyzed gelatine (BYCO-E) or synthetic polymer such as hydroxypropyl cellulose and the like. Most of the commercially available oil-soluble drug preparations are also provided by mixing or adsorbing directly, or are designed as dissolving, emulsifying or dispersing types. It is easy to those skilled in the art, therefore, to apply the process of such mixing, dissolving, emulsifying or dispersing types in the preparation of the ubidecarenone.

However, the difficulties in absorption of the ubidecarenone can not essentially be reduced, even when the preparations such as of dissolving, emulsifying or dispersing types in the prior art are designed.

Recently, much research for the micell formation of the oil soluble drugs such as ubidecarenone have been made in order to positively promote the lymphatic absorption thereof. The micell formation with hydrophilic surfactants such as Polysolvate-80, HCO-60, a bile salt, etc. have been reported, together with the experiments of absorption. As can be seen, in the above mentioned experiment using rats, the absorptivity is not improved, even if the bile salt is used, compared with that obtained by dissolving in sesame oil. When the HCO-60 is used, some extent of improvement can be seen, but this is not yet sufficient.

Additionally, among these hydrophilic surfactants, the bile salt is known to injure the mucous membrane of the stomach and the nonion surfactants may also injure the mucous membrane of the digestive tract.

From such standpoints, we have studied in many ways the ubidecarenone compositions to improve the absorption of the ubidecarenone, and have found that there is exhibited markedly improved absorptivity of the ubidecarenone, when it is administered together with a higher fatty acid, monoglyceride thereof, or a mixture thereof. Thus, this invention was accomplished.

The ways to promote the absorption of ubidecarenone in the prior art are, at the utmost, to use a composition containing a hydrophilic surfactant such as bile salt, HCO-60 etc. as a component. On the contrary, the present invention is characterized by the use of a composition containing hydrophobic higher fatty acid or lipophilic monoglyceride of fatty acid as the components. The absorption from the ubidecarenone composition of this invention is by far superior to that of the conventional ubidecarenone preparation.

The composition of this invention comprises the ubidecarenone and higher fatty acid(s) or monoglyceride(s) of higher fatty acid(s), or their mixture. The higher fatty acid can be a single compound or mixture of the acids. Either can be used in this invention. The monoglyceride of higher fatty acid can also be a single compound or mixture of the monoglycerides. Either can be used in this invention. A mixture of the higher fatty acid and monoglyceride of higher fatty acid can also be used. Said composition is novel, and it is impossible to assume such novel composition on the basis of the prior art.

The ubidecarenone, otherwise referred to as Coenzyme $Q_{10}$, is an effective drug for the remedy of coronary function and is widely used in the clinic.

The higher fatty acid used herein is a saturated or unsaturated fatty acid having 12 to 18 carbon atoms. Particularly effective acids are selected from unsaturated fatty acids such as oleic acid, linolic acid, linolenic acid and the like. Sodium salt(s) of higher fatty acid(s) may be used in place of the free fatty acid(s) according to this invention. In this case, the sodium salt(s) of higher fatty acid(s) are converted to the corresponding free fatty acid(s) through hydrolysis in the digestive tract. Therefore, said salt(s) provide, in fact, the same results as given by the higher fatty acid(s).

The monoglycerides of higher fatty acid have previously been used as lipophilic surfactants in the processing of foodstuffs. As described above, it is known in the prior art to improve the absorption of ubidecarenone using a hydrophilic surfactant for micell formation, but it is not known to increase the absorption of ubidecarenone through the lymphatic duct, using monoglyceride of higher fatty acid which is a lipophilic surfactant contrary to a hydrophilic surfactant.

Referring to monoglyceride of higher fatty acid to be used with this invention, there are used the fatty acids containing 12 to 18 carbon atoms, and particularly effective are unsaturated fatty acids such as oleic acid, linolic acid, linoleic acid and the like.

The higher fatty acid and the monoglyceride of higher fatty acid may be replaced by each other. Therefore, when a mixture of the higher fatty acid and the monoglyceride of higher fatty acid are used as the component of the composition according to this invention, any component ratio thereof may be employed without any limitation.

The component ratio of the higher fatty acid or the monoglyceride of the higher fatty acid or mixture thereof to one part of ubidecarenone is required to be 0.2 parts or more. Absorption experiments show that although the absorption increases in accordance with increase of the component ratio, there can not be observed a great change in the absorption beyond the ratio of 1.0 part.

In mixing the components to form the composition, the respective components may be directly mixed, or kneaded in solid state. They may be kneaded after melted. The composition may be also formed by the spray-drying process. The ubidecarenone is also combined with the higher fatty acid, the monoglyceride of higher fatty acid or their mixture, after it has been once adsorbed to excipients such as a micro crystalline cellulose, silica and the like.

Additives may be used if required. Illustrative of said additives include a micro crystalline cellulose, silica, corn starch, hydroxypropyl cellulose, lactose, gum arabic, hydrolyzed gelatin, etc.

The composition according to this invention may not only be in a form of powder, but also may be optionally formed into granules by adding binder; into tablets by compression; or into capsules by filling the powder or granules into a capsule.

Alternatively, it may be formed into a soft capsule by filling, into the capsule, oily components containing an oily higher fatty acid or a monoglyceride of higher fatty acid, or their mixture.

The following experiments will illustrate the effect of the composition according to this invention on the lymphatic absorption of ubidecarenone.

I. PREPARATION OF SAMPLE

Control sample 1

Ubidecarenone (one part) was melted in a mortar warmed on a water bath at 60° C. Microcrystalline cellulose (44 parts) was by portions added to the melted material with homogeneous mixing, to afford the sample.

Control sample 2

Hydroxypropyl cellulose (one part) was dissolved in a small quantity of water and heated to 60° C. Into this solution was added ubidecarenone (one part) melted at 60° C., to disperse the whole homogeneously. Lactose (44 parts) was, little by little, added to the dispersion. The mixture was homogeneously mixed and dried to afford the sample.

Control sample 3

Ubidecarenone (one part) melted at 60° C. was dissolved in sesame oil (30 parts) warmed to 60° C. To this solution was, by portions, added microcrystalline cellulose (44 parts). The mixture was homogeneously mixed to afford the sample.

The above-indicated control samples were prepared to be compared with the subject samples (specimen) of this invention, with respect to their effects. They contain ubidecarenone alone which was adsorbed to the excipient directly (the case of the control sample 1), in dispersion (the case of the control sample 2), or in solution (the case of the control sample 3).

On the other hand, the following specimens are related to the subject matter of this invention.

Specimen 1

Ubidecarenone (one part) melted at 60° C. was mixed with monoglyceride of oleic acid (30 parts) warmed to 60° C. To this mixture was, by portions, added microcrystalline cellulose (44 parts). The mixture was homogeneously mixed to afford the sample.

Specimen 2

Ubidecarenone (one part) melted at 60° C. was mixed with monoglyceride of linolenic acid (30 parts) warmed to 60° C. To this mixture was, by portions added microcrystalline cellulose (44 parts). The mixture was homogeneously mixed to afford the sample.

Specimen 3

Ubidecarenone (one part) melted at 60° C. was mixed with monoglyceride of palmitic acid (30 parts) warmed to 80° C. To this mixture was, by portions, added microcrystalline cellulose (44 parts). The mixture was homogeneously mixed to afford the sample.

Specimen 4

Ubidecarenone (one part) melted at 60° C. was mixed with oleic acid (30 parts) warmed to 60° C. To this mixture was, by portions, added microcrystalline cellulose (44 parts). The mixture was homogeneously mixed to afford the sample.

The following specimens were prepared in the similar manner according to the procedure as described in Specimen 1, except that the content of the monoglyceride of oleic acid was varied.

Specimen 1-A

This specimen was prepared according to the procedure as described in Specimen 1, except that the content of the monoglyceride of oleic acid was replaced with 0.2 parts.

Specimen 1-B

This specimen was prepared according to the procedure as described in specimen 1, except that the content of the monoglyceride of oleic acid was replaced with 0.5 parts.

Specimen 1-C

This specimen was prepared according to the procedure as described in specimen 1, except that the content of the monoglyceride of oleic acid was replaced with one part.

Specimen 1-D

This specimen was prepared according to the procedure as described in Specimen 1, except that the content of the monoglyceride of oleic acid was replaced with 5 parts.

Specimen 1-E

This specimen was prepared according to the procedure as described in Specimen 1, except that the content of the monoglyceride of oleic acid was replaced with 10 parts.

Specimen 1-F

This specimen was prepared according to the procedure as described in Specimen 1 except that the content of the monoglyceride of oleic acid was replaced with 50 parts.

II. PROCEDURES FOR ABSORPTION EXPERIMENT

1. Animals used for the experiment

Male rats of Wister strain (weighing 250–300 g), cannulated to the thoratic ducts having more than 20 ml of lymph flow rate during 20 hours in Bollman cages.

2. Absorption experiment (1) The respective amounts of 75 mg (corresponding to 1 mg of ubidecarenone) of the above-mentioned samples were weighed in a spitz roll, and water (0.5 ml) was added thereto to disperse the same. These dispersions were orally administered through a catheter into the rats which were previously fasted for 15 hours, although physiological saline solution was supplied without restraint.

(2) The absorption experiment was carried out according to the modified cross-over method as follows:

Three different samples were separately administered to the three rats; the combinations of the samples and rats were changed every day; at the last day the same samples as those administered at first were again administered in order to confirm no variation in the absorptivity during the experiment period. The average value was determined from the absorption experiments of six rats in total for each sample.

3. Quantitative analysis

Ubidecarenone was extracted from the collected lymph and determined by measuring absorption of UV of 275 mμ through a high velocity liquid chromatography (packing: Nucleosil C-18, developing solvent: 100% ethanol, column: 25 cm×0.46 cm in diameter, flow rate: 1.5 ml/min).

Since the lymph contains inherent endogenous ubidecarenone from the organism, determinations were made first for said inherent ubidecarenone before oral administration, and then for the ubidecarenone after oral administration, thereby correcting the latter data.

III. RESULTS

1. The following Table 1 shows the percent of lymphatic absorptivity of ubidecarenone 24 hours after the oral administration of controls 1-3 and specimens 1-5.

TABLE 1

| Sample | Components and ratio thereof | | Absorptivity through the lymphatic duct (%)[e] |
|---|---|---|---|
| Control 1 | Ubidecarenone | 1 | 2.28(1.89-2.66)% |
| | Micro crystalline cellulose | 44 | |
| Control 2 | Ubidecarenone | 1 | 2.96(1.95-4.26)% |
| | HPC-L[a] | 1 | |
| | Micro crystalline cellulose | 44 | |
| Control 3 | Ubidecarenone | 1 | 2.71(1.99-3.17)% |
| | Sesame oil | 30 | |
| | Micro crystalline cellulose | 44 | |
| Specimen 1 | Ubidecarenone | 1 | 7.56(4.95-9.15)% |
| | Monoolein[b] | 30 | |
| | Micro crystalline cellulose | 44 | |
| Specimen 2 | Ubidecarenone | 1 | 6.71(6.28-7.59)% |
| | Monolinolein[c] | 30 | |
| | Micro crystalline cellulose | 44 | |
| Specimen 3 | Ubidecarenone | 1 | 5.53(4.53-6.97)% |
| | Monopalmitin[d] | 30 | |
| | Micro crystalline cellulose | 44 | |
| Specimen 4 | Ubidecarenone | 1 | 8.17(6.63-9.41)% |
| | Oleic acid | 30 | |
| | Micro crystalline cellulose | 44 | |

Note:
[a] HPC-L: Hydroxypropyl cellulose-L
[b] Monoolein: Monoglyceride of oleic acid
[c] Monolinolein: Monoglyceride of linolenic acid
[d] Monopalmitin: Monoglyceride of palmitic acid
[e] The absorptivities (%) through the lymphatic duct show the average values given by 6 rats. The lower limit and the upper limit are shown in the parenthesis.

2. Absorptivities through the lymphatic duct for 24 hours after the oral administration of Specimens 1-A to 1-F and Specimen 1 are shown in the following Table 2.

TABLE 2

| Sample | Components and ratio thereof | | Absorptivity through the lymphatic duct (%)[a] |
|---|---|---|---|
| Specimen 1-A | Ubidecarenone | 1 | 3.74 |
| | Monoolein | 0.2 | |
| | Micro crystalline cellulose | 44 | |
| Specimen 1-B | Ubidecarenone | 1 | 4.89 |
| | Monoolein | 0.5 | |
| | Micro crystalline cellulose | 44 | |
| Specimen 1-C | Ubidecarenone | 1 | 5.50 |
| | Monoolein | 1 | |
| | Micro crystalline cellulose | 44 | |
| Specimen 1-D | Ubidecarenone | 1 | 6.10 |
| | Monoolein | 5 | |
| | Micro crystalline cellulose | 44 | |
| Specimen 1-E | Ubidecarenone | 1 | 5.58 |
| | Monoolein | 10 | |
| | Micro crystalline cellulose | 44 | |
| Specimen 1 | Ubidecarenone | 1 | 6.80 |
| | Monoolein | 30 | |
| | Micro crystalline cellulose | 44 | |
| Specimen 1-F | Ubidecarenone | 1 | 6.08 |
| | Monoolein | 50 | |
| | Micro crystalline cellulose | 44 | |

Note:
[a] Absorptivity (%) through the lymphatic duct is shown in the average values given by two rats.

Following examples will illustrate more particularly this invention. It should be understood that the examples are merely illustrative and are not presented as a definition of the limit of the invention.

EXAMPLE 1

Ubidecarenone (4 g) and monoolein (28 g) were weighed in a mortar, and the whole was melted to mix on a water bath at about 60° C. To the mixture were added micro crystalline cellulose (68 g), followed by grinding the same, to provide ubidecarenone powder.

EXAMPLE 2

Ubidecarenone (1 g) was melted on a water bath at about 60° C., and mixed with oleic acid (49 g), to provide a ubidecarenone solution in oleic acid.

EXAMPLE 3

Gum arabic (150 g) was dissolved in distilled water (1 liter). Lactose (290 g) was added to the solution. The solution was heated to 60° C.

Ubidecarenone (10 g) was separately added to linolic acid (50 g), and the mixture was warmed on a water bath at 60° C. to dissolve the same. The gum arabic solution was stirred using Polytron, and emulsified with slow addition of the ubidecarenone solution in linolic acid. The emulsion was spray-dried by a spray-dryer of rotary disc type, to provide emulsifiable ubidecarenone powder.

EXAMPLE 4

The ubidecarenone powder (125 g) prepared according to the procedure in Example 1 was homogeneously mixed with corn starch (54 g) and calcium stearate (1 g). Each aliquot (180 mg) of the mixture was filled in No. 3 hard capsule.

EXAMPLE 5

The solution of ubidecarenone in oleic acid prepared according to the procedure in Example 2 was filled in soft capsules.

EXAMPLE 6

Ubidecarenone (5 g) and monoolein (25 g) were melted and mixed on a water bath at about 60° C. The mixture was homogeneously adsorbed to micro crystalline cellulose (60 g), followed by mixing with lactose (57 g) and corn starch (20 g). The mixed powder was kneaded with an ethanol solution of HPC-L (10 g). The resulting mixture was granulated using granulator through a screen of 0.7 mm diameter. The granules were dried at 40° C., followed by screening with a screen of 20 meshes. After adding CMC (10 g) to the granules, there was added calcium stearate (0.5 g) and talc (2.5 g) through a screen of 80 meshes, and the whole was mixed homogeneously. The mixture was compressed into the tablets, each having diameter 8 mm, and weighing 190 mg.

EXAMPLE 7

Ubidecarenone (10 g) and monoolein (20 g) were heated to melt on a water bath at about 60° C. The mixture was homogeneously adsorbed to micro crystalline cellulose (100 g), followed by mixing with lactose (730 g) and corn starch (100 g). The mixture was kneaded with an ethanol solution of HPC-L (40 g). The resulting mixture was granulated using a cylindrical granulator through a screen of diameter 0.5 mm. The granules were dried at 40° C. followed by screening to afford the granule preparation.

EXAMPLE 8

Ubidecarenone (4 g), monoolein (14 g) and oleic acid (14 g) were weighed in motar, and the whole was melted to mix on a water bath at about 60° C. To the mixture were added microcrystalline cellulose (68 g), followed by grinding the same, to provide ubidecarenone powder.

What is claimed is:

1. An orally administrable composition for the treatment of hypertensive disease which comprises ubidecarenone in admixture with not less than 0.2 parts per 1 part by weight of ubidecarenone of a higher fatty acid having 12 to 18 carbon atoms, a monoglyceride of a higher fatty acid having 12 to 18 carbon atoms or a mixture thereof.

2. A composition according to claim 1 which contains a higher saturated or unsaturated fatty acid having 12 to 18 carbon atoms.

3. A composition according to claim 1 which contains a monoglyceride of a higher saturated or unsaturated fatty acid having 12 to 18 carbon atoms.

4. A composition according to claim 1 wherein a higher fatty acid is used in the form of the sodium salt thereof.

* * * * *